(12) United States Patent
Tollini et al.

(10) Patent No.: US 10,525,196 B2
(45) Date of Patent: Jan. 7, 2020

(54) SECUREMENT DEVICE

(71) Applicant: TNT Moborg International Limited, Williamsville, NY (US)

(72) Inventors: Dennis R. Tollini, Clarence Center, NY (US); Michael D. Tollini, Clarence Center, NY (US)

(73) Assignee: TNT Moborg International Limited, Williamsville, NY (US)

( * ) Notice: Subject to any disclaimer, the term of this patent is extended or adjusted under 35 U.S.C. 154(b) by 399 days.

(21) Appl. No.: 15/235,938

(22) Filed: Aug. 12, 2016

(65) Prior Publication Data

US 2018/0043092 A1 Feb. 15, 2018

(51) Int. Cl.
*A61M 5/158* (2006.01)

(52) U.S. Cl.
CPC ..... *A61M 5/158* (2013.01); *A61M 2005/1586* (2013.01)

(58) Field of Classification Search
CPC .......... A61M 2005/1586; A61M 5/158; A61M 2025/0253
See application file for complete search history.

(56) References Cited

U.S. PATENT DOCUMENTS

| | | | |
|---|---|---|---|
| 3,288,136 A | 11/1966 | Lund | |
| 3,826,254 A | 7/1974 | Mellor | |
| 3,834,380 A | 9/1974 | Boyd | |
| 4,665,566 A * | 5/1987 | Garrow | A61M 16/0666 128/201.22 |
| 4,702,736 A | 10/1987 | Kalt et al. | |
| 4,738,662 A | 4/1988 | Kalt et al. | |
| 4,838,878 A | 6/1989 | Kalt et al. | |
| 4,976,700 A * | 12/1990 | Tollini | A61M 25/02 128/877 |
| 5,037,397 A | 8/1991 | Kalt et al. | |
| 5,098,399 A | 3/1992 | Tollini | |
| 5,147,322 A * | 9/1992 | Bowen | A61M 25/02 128/DIG. 26 |
| 5,266,401 A | 11/1993 | Tollini | |
| 5,300,037 A | 4/1994 | Delk et al. | |
| 5,304,146 A * | 4/1994 | Johnson | A61M 25/02 128/DIG. 26 |
| 5,520,656 A | 5/1996 | Byrd | |
| 5,575,802 A | 11/1996 | McQuilkin et al. | |
| 5,681,290 A | 10/1997 | Alexander | |
| 6,419,660 B1 * | 7/2002 | Russo | A61M 25/02 128/DIG. 26 |
| 6,689,105 B2 | 2/2004 | Tollini | |
| 9,486,613 B2 * | 11/2016 | Dickert | A61M 25/02 |
| 2002/0156423 A1 * | 10/2002 | Tollini | A61M 25/02 604/180 |

* cited by examiner

*Primary Examiner* — Quynh-Nhu H. Vu
(74) *Attorney, Agent, or Firm* — Simpson & Simpson, PLLC

(57) ABSTRACT

A securement device, comprising a first tape having a first top surface and a first bottom surface, a second tape having a second top surface and a second bottom surface, the second bottom surface at least partially connected to the first bottom surface, a first adhesive pad secured to the first top surface at a first location, and a second adhesive pad at least partially secured to the first top surface at a second location.

9 Claims, 5 Drawing Sheets

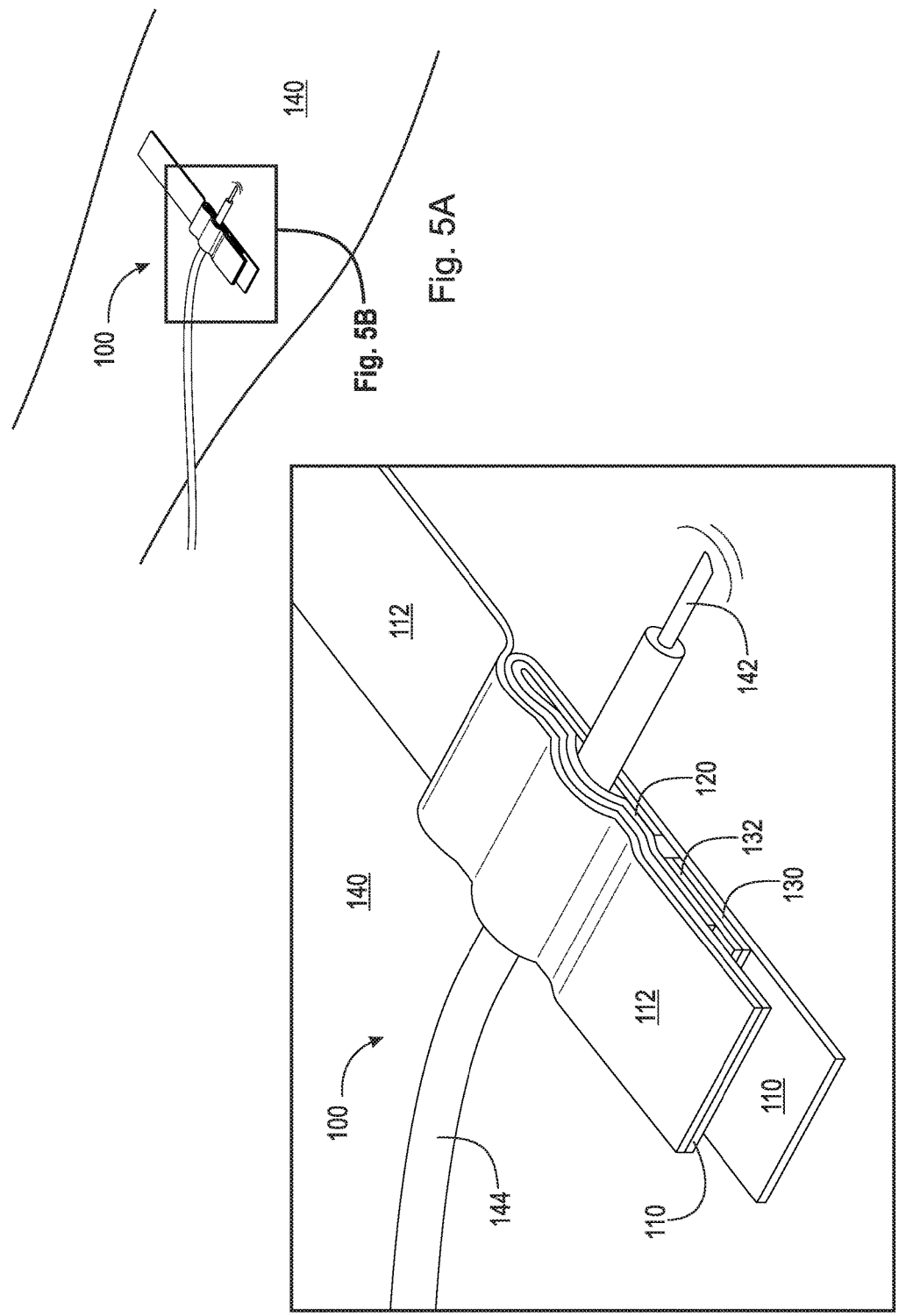

SECUREMENT DEVICE

FIELD

The disclosure broadly relates to securement devices, and, more particularly to securement devices for securing medical devices to patients.

BACKGROUND

Securement devices are used in the medical profession to secure needles, catheters, and catheters with extension sets inserted within patients to prevent dislodgement, phlebitis, damage to surrounding tissue, and the ingress of bacteria at the insertion site. Medical grade tape can be used as a securement device or to supplement a securement device. Safe and effective securement devices are particularly critical for the treatment of chronic conditions, such as kidney failure, which requires frequent dialysis treatment for removing waste from a patient's blood. For a patient receiving routine hemodialysis, for example, a temporary access catheter is one method that may be used to gain access to the blood. Catheter access consists of a catheter with two lumens which is inserted into a large vein to allow large flows of blood to be withdrawn from one lumen, to enter the dialysis circuit, and to be returned via the other lumen. In another method of dialysis, peritoneal dialysis, a patient has a surgically inserted catheter that then is attached to an extension set. That patient infuses a dextrose solution into their peritoneal sac and the peritoneal membrane allows for osmotic removal into the dextrose solution, which provides normal kidney function to occur.

To expedite hemodialysis which can take hours to complete, efficient blood and dialysate flow rates are desired. To achieve optimal flow rates, needles or catheters often require adjustment, either at the onset of or at some point during treatment. Typically, to adjust a securement device, tape is removed and new tape is applied to and around the site further aggravating the skin.

Healthcare providers have struggled with providing securement devices that are effective and sterile yet minimally aggravating to patients.

Expired U.S. Pat. No. 4,702,736 (Kalt I) discloses a clamp for holding an article to an object including a base means for adhering the clamp to the object, a flap, securing means for securing the flap to the base means with the article positioned there between and resilient pad means having an adhesive surface for contacting the article. The securing means includes a first holding means for holding a first portion of the flap and a second holding means for holding a second portion of the flap. Both holding means may be releasable. The second holding means is spaced from the first holding means a sufficient distance along the flap for the article to lie between them. Resilient adhesive surfaces are provided on the flap and base means for contacting and adhering the article. However, the Kalt I reference discloses one continuous piece as a bottom base which can still potentially cause movement and discomfort near the insertion site.

Expired U.S. Pat. No. 4,738,662 (Kalt II) discloses a clamp similar to that of Kalt I, but adds a second clamp for holding an article to an object including a bottom base means for adhering the clamp to an object, a top flap with a slit, a resilient adhesive pad, and securing means for securing the flap to the base means with the article passing through the slit in the flap and perpendicular to the base. The securing means includes a first holding means and a second holding means for holding the top flap and bottom base. Both holding means may be releasable. The clamp comprises a top flap with a slit to create two sections of the first portion of the securing means, one section on each side of the slit. The second holding means is on the bottom base. The first and second holding means are removably connected. The slit allows an object to pass through the clamp where it will adhesively connect to a resilient adhesive pad located on the top flap. Kalt II discloses that, in the preferred embodiment, the slit provides stability for a tube upon exiting the nasal passage way to extend upward along the bridge of the nose. The Kalt II reference discloses a second clamp to be used in combination with the Kalt I reference. However, the second clamp disclosed in the Kalt II reference introduces a slit to allow the tube to pass directly through the flap in order to extend upwardly.

There is a long-felt need for a for a securement device that can easily attach and secure needles, catheters, and catheters with extension sets inserted within a patient to prevent damage to surrounding tissue, dislodgment, and infection at the insertion site.

Therefore, there is a long-felt need for a securement device for securing medical devices to patients that connects the bottom of the flap when folded over, now on top, to the base in order to provide a high level of stability and create the least amount of stress near an insertion site.

SUMMARY

According to aspects illustrated herein, there is provided a securement device, comprising a first tape having a first top surface and a first bottom surface, a second tape having a second top surface and a second bottom surface, the second bottom surface at least partially connected to the first bottom surface, a first adhesive pad secured to the first top surface at a first location, and a second adhesive pad at least partially secured to the first top surface at a second location.

According to aspects illustrated herein, there is provided a securement device, comprising a first tape having a first top surface and a first bottom surface, a second tape having a second top surface and a second bottom surface, the second top surface at least partially connected to the first bottom surface, a third tape having a third top surface and a third bottom surface, the third bottom surface at least partially connected to the second bottom surface, a first adhesive pad secured to the first top surface, and a second adhesive pad at least partially secured to the second top surface.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which:

FIG. 5A is a perspective view of the securement device shown in FIG. 1 securing a needle within a patient's arm; and, FIG. 5B is a detail view of the securement device shown in FIG. 5A.

DETAILED DESCRIPTION OF THE DRAWINGS

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

Figure 1:
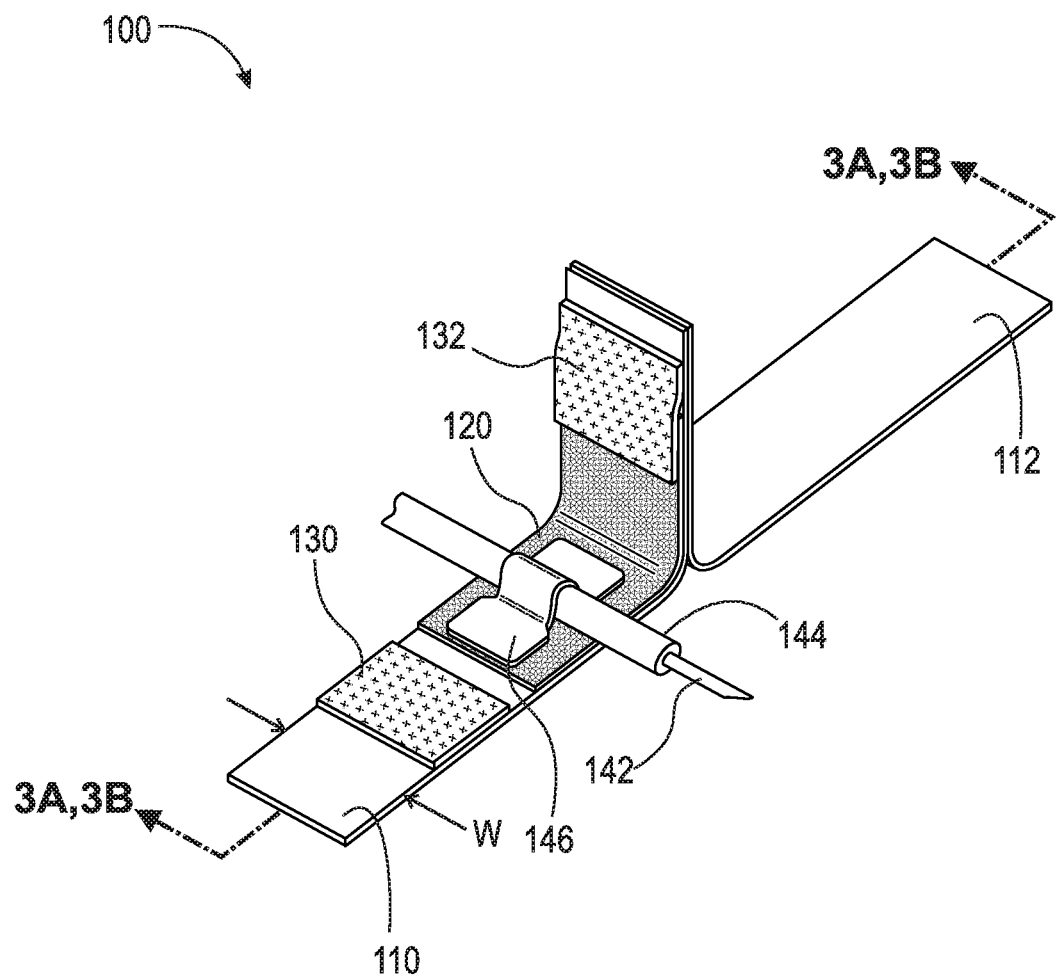
FIG. 1 is a top perspective view of a securement device.

It should be appreciated that the thickness of the components shown in the Figures is exaggerated for clarity. Adverting now to the figures, FIG. 1 is a top perspective view of securement device 100. Securement device 100 comprises tape 110, tape 112, tape 120, adhesive pad 130, and adhesive pad 132. In this exemplary embodiment, tape 110, tape 112, tape 120, adhesive pad 130, and adhesive pad 132 are all substantially rectangular. It should be appreciated that in another embodiment, tape 110, tape 112, tape 120, adhesive pad 130, and adhesive pad 132 can be any geometric shape suitable for securing a needle in a patient's arm (e.g., triangle, parallelogram, circle, etc.). As shown in FIG. 1, the width of tape 110 is equal to the width of tape 112, for example, width W. In another embodiment, tape 110 may have a width that is greater than or less than the width of tape 112. The width of tape 120, adhesive pad 130, and adhesive pad 132, is equal to the width of tape 110, for example, width W, which provides the best adhesive qualities to secure needle 142 (see FIGS. 5A and 5B). In an example embodiment, tape 120 is split up into two separate strips (i.e., long, skinny rectangles), that are each less than one half of width W.

Figure 2:
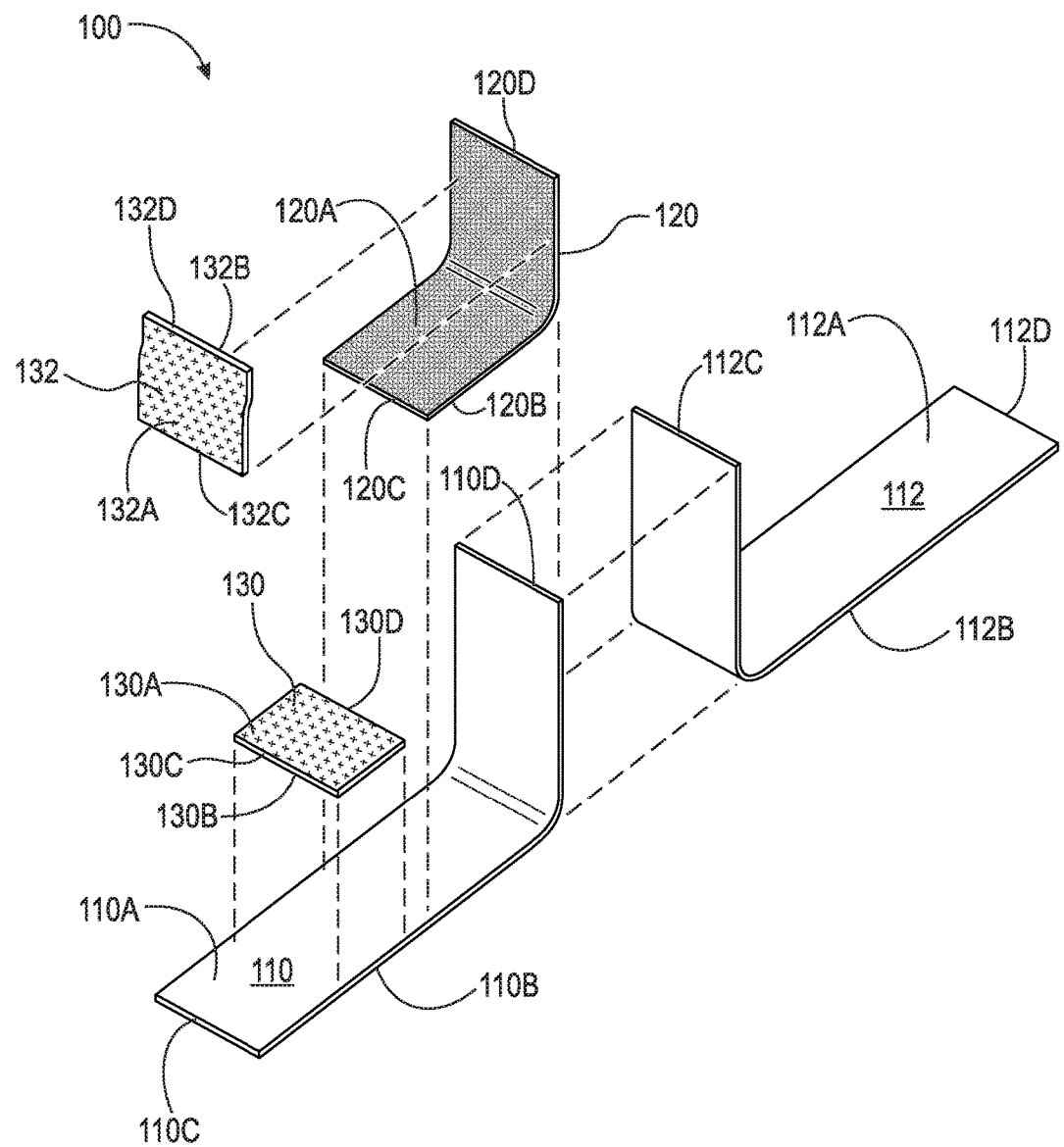
FIG. 2 is an exploded view of the securement device in FIG. 1.

FIG. 2 is an exploded view of securement device 100 as shown in FIG. 1. Tape 110 comprises top 110A, bottom surface 110B, side 110C, and side 110D. Tape 112 comprises top surface 112A, bottom surface 112B, side 112C, and side 112D. Tape 120 comprises top surface 120A, bottom surface 120B, side 120C, and side 120D. Adhesive pad 130 comprises top surface 130A, bottom surface 130B, side 130C, and side 130D. Adhesive pad 132 comprises top surface 132A, bottom surface 132B, side 132C, and side 132D. Tape 110, tape 112, tape 120, adhesive pad 130, and adhesive pad 132 comprise at least one adhesive layer, for example, on bottom surfaces 110B, 112B, 120B, 130B, and 132B, respectively. Adhesive pads 130 and 132 comprise an adhesive material, for example Velcro® hook-and-loop fastener, on top surfaces 130A and 132A, respectively. It should be appreciated, however, that adhesive pads 130 and 132 can be any material suitable for connecting and disconnecting to each other repeatedly. In addition, tape 120 comprises a second adhesive layer on top surface 120A.

Figure 3A:
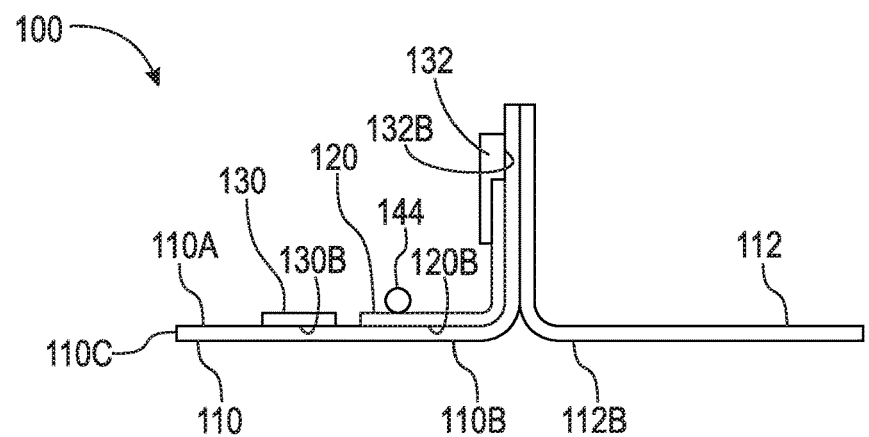
FIG. 3A is a cross-sectional view of the securement device in FIG. 1, taken generally along line 3A-3A.

FIG. 3A is a cross-sectional view of securement device 100 taken generally along line 3A-3A in FIG. 1. Tape 110 is at least partially secured to tape 112, for example, by securing bottom surface 110B to bottom surface 112B, creating a flap. Tape 120 is secured to tape 110, for example, by securing bottom surface 120B to top surface 110A. Adhesive pads 130 and 132 are secured to tape 110, for example, by securing bottom surfaces 130B and 132B to top surface 110A, respectively. Adhesive pad 132 may also be partially secured to tape 120, for example, by securing bottom surface 132B to top surface 120A.

Figure 3B:
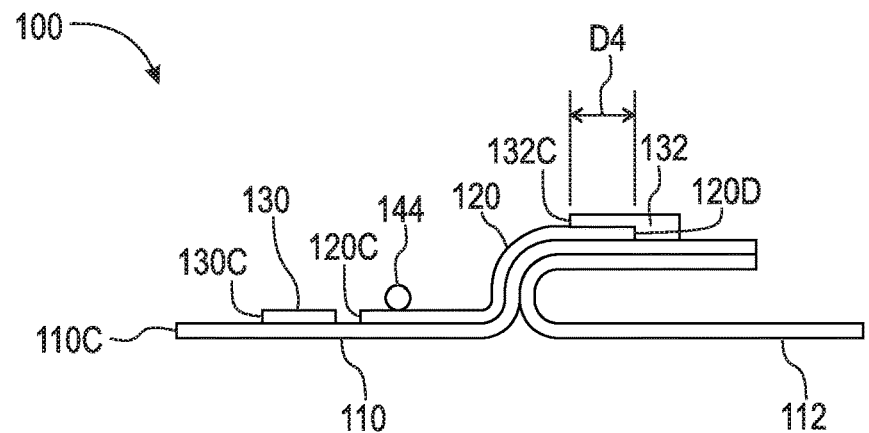
FIG. 3B is a cross-sectional view of the securement device in FIG. 1, taken generally along line 3B-3B.
Figure 3C:
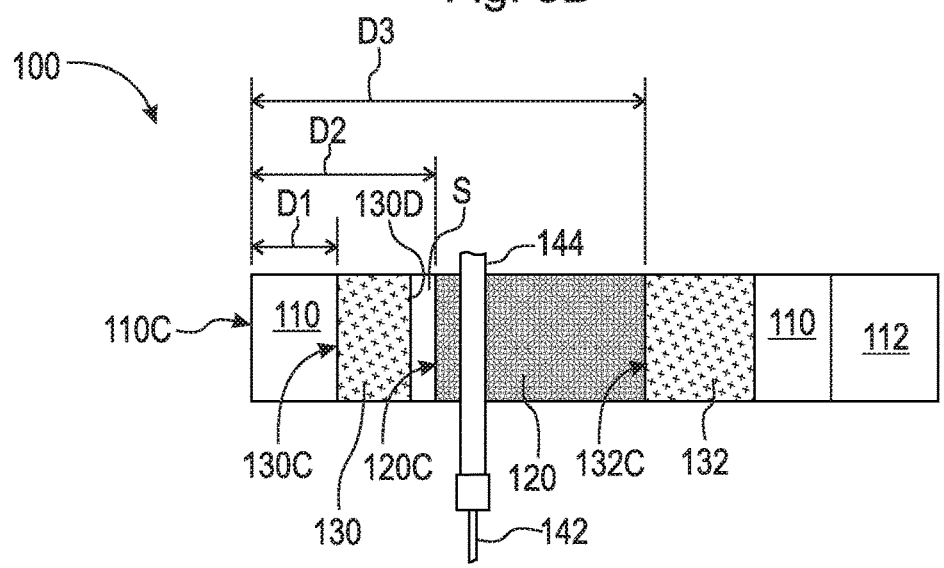
FIG. 3C is a top planar view of the securement device in FIG. 3B.

FIG. 3B is a cross-sectional view of securement device 100 taken generally along line 3B-3B in FIG. 1, with tape 110 in a fully opened position (i.e. extended over tape 112). FIG. 3C is a top planar view of securement device 100 as shown in FIG. 3B. Adhesive pad 130 is to secured tape 110 such that side 130C is distance D1 from side 110C. Tape 120 is secured to tape 110 such that side 120C is distance D2 from side 110C. Adhesive pad 132 is secured to tape 110 such that side 132C is distance D3 from side 110C. Distance D3 is greater than distance D2, and distance D2 is greater than distance D1. Securement device 100 is assembled such that side 120C is separated from side 130D by space S, and side 132C overlaps side 120D by distance D4. It should be appreciated, however, that side 120C does not need to be separated from side 130D by space S, but that side 120C can abut against or overlap side 130D.

Figure 4:
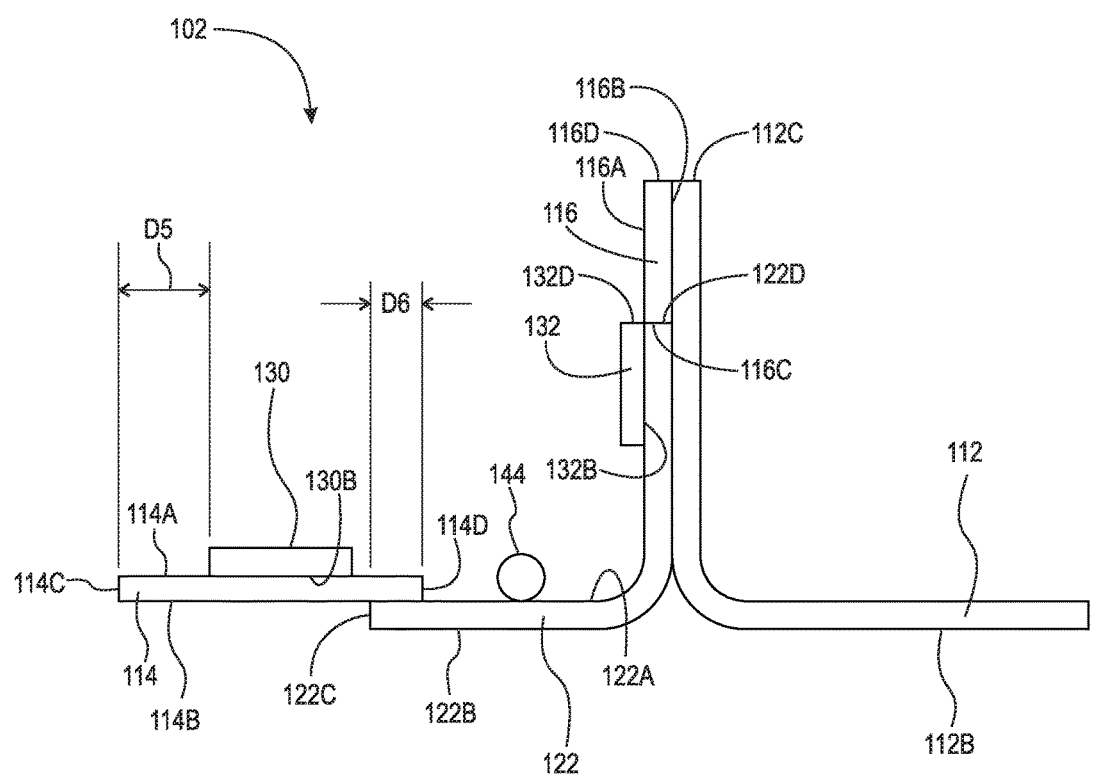
FIG. 4 is a cross-sectional view of a securement device.

FIG. 4 is a cross-sectional view of securement device 102. Securement device 102 comprises tape 114, tape 112, tape 116, tape 122, adhesive pad 130, and adhesive pad 132. Tape 114, tape 112, tape 116, tape 122, adhesive pad 130, and adhesive pad 132 are all substantially rectangular. It should be appreciated that in an example embodiment, tape 114, tape 112, tape 116, tape 122, adhesive pad 130, and adhesive pad 132 can be any geometric shape suitable for securing a needle in a patient (e.g., triangle, parallelogram, circle, etc.). The width of tape 114 and tape 116 is equal to the width of tape 112. In an example embodiment, tape 114 and tape 116 may have a width that is greater than or less than the width of tape 112. The width of tape 122, adhesive pad 130, and adhesive pad 132, is equal to the width of tape 114, which provides the best adhesive qualities to secure needle 142. In an example embodiment, tape 122 is split up into two separate strips (i.e., long, skinny rectangles), that are each less than one half of the width of tape 114.

Tape 114 comprises top 114A, bottom surface 114B, side 114C, and side 114D. Tape 112 comprises top surface 112A, bottom surface 112B, side 112C, and side 112D. Tape 116 comprises top surface 116A, bottom surface 116B, side 116C, and side 116D. Tape 122 comprises top surface 122A, bottom surface 122B, side 122C, and side 122D. Adhesive pad 130 comprises top surface 130A, bottom surface 130B, side 130C, and side 130D. Adhesive pad 132 comprises top surface 132A, bottom surface 132B, side 132C, and side 132D. Tape 114, tape 112, tape 116, tape 122, adhesive pad 130, and adhesive pad 132 comprise at least one adhesive layer, for example, on bottom surfaces 114B, 112B, 116B, 122B, 130B, and 132B, respectively. Adhesive pads 130 and 132 comprise an adhesive material, for example Velcro® hook-and-loop fastener, on top surfaces 130A and 132A, respectively. It should be appreciated, however, that adhesive pads 130 and 132 can be any material suitable for connecting and disconnecting to each other repeatedly. In addition, tape 122 comprises a second adhesive layer on top surface 122A.

Tape 114 is at least partially secured to tape 122, for example, by securing bottom surface 114B to top surface 122A. Tape 122 is at least partially secured to tape 112, for example, by securing bottom surface 122B to bottom surface 112B, creating a flap. Adhesive pad 130 is secured to tape 114, for example, by securing bottom surface 130B to top surface 114A. Adhesive pad 132 is secured to tape 122, for example, by securing bottom surface 132B to top surface 122A. In an example embodiment, adhesive pad 132 may also be partially secured to tape 112, for example, by securing bottom surface 132B to top surface 120A. Tape 116 is secured to tape 112, for example, by securing bottom surface 116B to bottom surface 112B.

Adhesive pad 130 is to secured tape 114 such that side 130C is distance D5 from side 114C. Tape 114 is secured to tape 122 such that side 114D is distance D6 from side 122C. Adhesive pad 132 is secured to tape 122 such that side 132D aligns with side 122D. It should be appreciated, however, that in an example embodiment side 132D can extend past side 122D such that adhesive pad 132 is also partially secured to tape 112, for example, by securing bottom surface 132B partially to top surface 122A as well as partially to bottom surface 112B. Tape 116 is secured to tape 112 such that side 116D aligns with side 112C.

FIG. 5A is a perspective view of needle 142 inserted in patient's arm 140 with securement device 100 in the closed position. FIG. 5B is a detail view of securement device 100 as shown in FIG. 5A. Tapes 110 and 112 are at least partially secured to patient's arm 140, for example, by partially securing bottom surfaces 110B and 112B to the patient's skin. It should be appreciated that in the closed position, tube 144 fully passes through securement device 100, while adhesively connecting to tape 120. Adhesive pad 132 is secured to adhesive pad 130, for example, by securing top surface 132A to top surface 130A. Top surface 120A comprises an adhesive layer and is enclosed around tube 144, thus securing needle 142 within patient's arm 140. This connection decreases the movement of tube 144 and increases overall stability of needle 142 within patient's arm 140. It should be appreciated that securement device 102 functions substantially the same as securement device 100 as shown in FIGS. 5A and 5B.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

100 Securement device
102 Securement device
110 Tape
110A Top surface
110B Bottom surface
110C Side
110D Side
112 Tape
112A Top surface
112B Bottom surface
112C Side
112D Side
114 Tape
114A Top surface
114B Bottom surface
114C Side
114D Side
116 Tape
116A Top surface
116B Bottom surface
116C Side
116D Side
120 Tape
120A Top surface
120B Bottom surface
120C Side
120D Side
122 Tape
122A Top surface
122B Bottom surface
122C Side
122D Side
130 Adhesive pad
130A Top surface
130B Bottom surface
130C Side
130D Side
132 Adhesive pad
132A Top surface
132B Bottom surface
132C Side
132D Side
140 Patient's arm
142 Needle
144 Tube
146 Wings
D1 Distance 1
D2 Distance 2
D3 Distance 3
D4 Distance 4
D5 Distance 5
D6 Distance 6
S Space
W Width

What is claimed is:

1. A securement device, comprising:
   a first tape having a first top surface, a first bottom surface, a first edge, and a second edge;
   a second tape having a second top surface and a second bottom surface, said second bottom surface at least partially connected to said first bottom;
   a third tape having a third top surface, a third bottom surface, and a third edge, said third bottom surface secured to the first top surface:
   a first adhesive pad secured to said first top surface; and,
   a second adhesive pad at least partially secured to said first top surface, wherein the second adhesive pad is spaced apart from the first edge and overlaps the third edge.

2. The securement device as recited in claim 1, wherein said first and second bottom surfaces comprise an adhesive layer.

3. The securement device as recited in claim 1, wherein said third top and bottom surfaces comprise an adhesive layer.

4. The securement device as recited in claim 1, wherein said first adhesive pad is spaced apart from said second edge.

5. The securement device as recited in claim 1, wherein said second adhesive pad is at least partially secured to said third top surface.

6. The securement device as recited in claim 1, wherein said first and second adhesive pads are capable of being removably connected.

7. The securement device as recited in claim 6, wherein said first adhesive pad and said second adhesive pad comprises hook-and-loop fastener.

8. A securement device, comprising:
a first tape having a first top surface, a first bottom surface, and a first edge;
a second tape having a second top surface and a second bottom surface, said second bottom surface at least partially connected to said first bottom surface;
a third tape having a third top surface, a third bottom surface, and a second edge, said third bottom surface secured to said first top surface in a third location;
a first adhesive pad secured to said first top surface at a first location, wherein a space is arranged between the second edge and the first adhesive pad; and,
a second adhesive pad at least partially secured to said first top surface and at least partially secured to said third top surface at a second location.

9. The securement device as recited in claim 8, wherein the second adhesive pad is spaced apart from the first edge.

* * * * *